US008609131B2

(12) United States Patent
Plaut et al.

(10) Patent No.: US 8,609,131 B2
(45) Date of Patent: *Dec. 17, 2013

(54) ABSORBENT DRESSING COMPRISING HYDROPHILIC POLYMER PREPARED VIA MICHAEL REACTION

(75) Inventors: David J. Plaut, Minneapolis, MN (US); Duane D. Fansler, Dresser, WI (US); Kevin M. Lewandowski, Inver Grove Heights, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1630 days.

This patent is subject to a terminal disclaimer.

(21) Appl. No.: 11/042,229

(22) Filed: Jan. 25, 2005

(65) Prior Publication Data

US 2006/0165762 A1 Jul. 27, 2006

(51) Int. Cl.
 A61L 15/00 (2006.01)
 C08G 63/00 (2006.01)
 C08L 33/08 (2006.01)
 C08L 33/10 (2006.01)
 C08L 71/02 (2006.01)

(52) U.S. Cl.
 USPC ........... 424/445; 424/487; 525/300; 525/303; 525/304; 525/305; 528/220

(58) Field of Classification Search
 None
 See application file for complete search history.

(56) References Cited

U.S. PATENT DOCUMENTS

| | | |
|---|---|---|
| 2,730,517 A | 1/1956 | Vogel et al. |
| RE24,906 E | 12/1960 | Ulrich |
| 3,121,021 A | 2/1964 | Copeland |
| 3,389,827 A | 6/1968 | Abere et al. |
| 4,112,213 A | 9/1978 | Waldman |
| 4,262,072 A | 4/1981 | Wendling et al. |
| 4,379,201 A * | 4/1983 | Heilmann et al. ............. 428/345 |
| 4,408,018 A | 10/1983 | Bartman et al. |
| 4,499,896 A | 2/1985 | Heinecke |
| 4,598,004 A | 7/1986 | Heinecke |
| 4,680,352 A | 7/1987 | Janowicz et al. |
| 4,694,054 A | 9/1987 | Janowicz |
| 4,849,458 A | 7/1989 | Reed et al. |
| 4,871,822 A | 10/1989 | Brindöpke et al. |
| 5,132,367 A | 7/1992 | Chan |
| 5,362,826 A | 11/1994 | Berge et al. |
| 5,459,178 A | 10/1995 | Chan et al. |
| 5,466,863 A | 11/1995 | Heidt et al. |
| 5,531,855 A | 7/1996 | Heinecke et al. |
| 5,539,017 A | 7/1996 | Rheinberger et al. |
| 5,614,310 A | 3/1997 | Delgado et al. |
| 5,653,699 A | 8/1997 | Reed et al. |
| 5,733,570 A | 3/1998 | Chen et al. |
| 5,738,642 A | 4/1998 | Heinecke et al. |
| 5,773,534 A | 6/1998 | Antonelli et al. |
| 5,849,325 A | 12/1998 | Heinecke et al. |
| 6,025,410 A | 2/2000 | Moy et al. |
| 6,117,492 A * | 9/2000 | Goldstein et al. ............. 427/391 |
| 6,171,985 B1 | 1/2001 | Joseph et al. |
| 6,174,929 B1 * | 1/2001 | Hahnle et al. .................. 521/64 |
| 6,198,016 B1 | 3/2001 | Lucast et al. |
| 6,221,303 B1 | 4/2001 | Steinmann |
| 6,420,622 B1 | 7/2002 | Johnston et al. |
| 6,448,301 B1 | 9/2002 | Gaddam et al. |
| 6,479,073 B1 * | 11/2002 | Lucast et al. .................. 424/448 |
| 6,566,575 B1 | 5/2003 | Stickels et al. |
| 6,635,690 B2 | 10/2003 | Heilmann et al. |
| 6,664,306 B2 | 12/2003 | Gaddam et al. |
| 2001/0051178 A1 | 12/2001 | Blatchford et al. |
| 2002/0122771 A1 * | 9/2002 | Holland et al. ................. 424/43 |
| 2003/0083389 A1 * | 5/2003 | Kao et al. ....................... 516/98 |
| 2003/0203011 A1 * | 10/2003 | Abuelyaman et al. ........ 424/445 |
| 2003/0212210 A1 | 11/2003 | Heilmann et al. |
| 2003/0216519 A1 | 11/2003 | Heilmann et al. |
| 2005/0192370 A1 | 9/2005 | Fansler et al. |
| 2005/0194559 A1 | 9/2005 | Lewandowski et al. |

FOREIGN PATENT DOCUMENTS

| | | | |
|---|---|---|---|
| EP | 0 227 454 A2 | 7/1987 | |
| JP | 63194727 | * 8/1988 | ............... B01J 13/00 |
| WO | WO 95/16749 A1 | 6/1995 | |
| WO | WO 99/13865 A1 | 3/1999 | |
| WO | WO 99/13866 A1 | 3/1999 | |
| WO | WO 02/20625 A1 | 3/2002 | |
| WO | 02/102909 A1 | 12/2002 | |
| WO | WO 03/086493 A1 | 10/2003 | |
| WO | WO 2005/092402 A1 | 10/2005 | |

OTHER PUBLICATIONS

Rosén, O., et al. Langmuir (1998) 14; 777-782.*
Moszner et al., "*Polymer Network Formation by Michael Reaction of Multifunctional Acetoacetates with Multifunctional Acrylates*", Macromolecular Rapid Communications, (1995), pp. 135-138, vol. 16.
Gladyshev et al., "*Polymerization at Advanced Degrees of Conversion*", (1970), Keter Press, Jerusalem.
Odian, "*Principles of Polymerization*", (1991), p. 108, 3$^{rd}$ Edition, John Wiley & Sons, New York.
Rector et al., "*Applications for the Acetoacetyl Functionality in Thermoset Coatings*", Proceedings of the Fifteenth Water-Borne and Higher-Solids Coatings Symposium, (Feb. 3-5, 1988), pp. 68-93.
Trumbo, "*Michael Addition Polymers from 1,4 and 1,3 Benzenedimethanol Diacetoacetates and Tripropylene Glycol Diacrylate*", Polymer Bulletin, (1991), pp. 265-270, vol. 26.

(Continued)

*Primary Examiner* — Kevin S Orwig
(74) *Attorney, Agent, or Firm* — Kent S. Kokko

(57) ABSTRACT

An absorbent dressing is described which comprises a crosslinked hydrophilic gel absorbent layer comprising a first component polymer comprising a plurality of polymerized monomer units having pendent hydrophilic groups, and pendent Michael donor groups; and a crosslinking agent comprising at least two Michael acceptor groups.

15 Claims, No Drawings

(56) References Cited

OTHER PUBLICATIONS

Trumbo, "*Michael Addition Polymers from Bisacetoacetates II. 2,2-dimethyl-1,3-bis(acetoacetyl)-propanediol and N,N'-bis(acetoacetyl)-1,4-piperazine*", Polymer Bulletin, (1991), pp. 481-485, vol. 26.

Clemens, "*A Comparison of Catalysts for Crosslinking Acetoacetylated Resins via the Michael Reaction*", Journal of Coatings Technology, (Mar. 1989), pp. 83-91, vol. 61, No. 770.

Li et al., "*Use of Formic Acid in Controlling the Rate of the Michael Addition Reaction in Base Catalyzed, Thermally Cured Acetoacetylated Acrylic/TMPTA Coatings*", Journal of Coatings Technology, (Jun. 1993), pp. 63-69, vol. 65, No. 821.

Rector et al., "*Applications for Acetoacetyl Chemistry in Thermoset Coatings*", Journal of Coatings Technology, (Apr. 1989), pp. 31-37, vol. 61, No. 771.

Rector et al., "*Synthesis of Acetoacetylated Resins and Applications for Acetoacetate Chemistry in Thermoset Coatings*", Surface Coatings Australia, (Sep. 1989), pp. 6-15.

U.S. Appl. No. 10/792,238, filed Mar. 2, 2004, entitled "*Crosslinkable Hydrophilic Materials from Reactive Oligomers Having Pendent Unsaturated Groups*".

U.S. Appl. No. 10/956,841, filed Oct. 1, 2004, entitled "*Ring-Opened Azlactone Telechelic Polymer*".

\* cited by examiner

US 8,609,131 B2

ABSORBENT DRESSING COMPRISING HYDROPHILIC POLYMER PREPARED VIA MICHAEL REACTION

TECHNICAL FIELD OF THE INVENTION

This invention relates to novel hydrophilic, crosslinkable polymer compositions and articles prepared therefrom. The compositions can be useful in preparing gel materials and medical articles incorporating such materials, particularly medical articles useful as wound dressings.

BACKGROUND OF THE INVENTION

Historically, exudate from a wound has been treated by absorbing it using a dressing containing an absorbent material. Such dressings have contained a padded absorbent material attached to an adhesive tape backing. The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material Some current wound care products use a hydrocolloid absorbent. Such materials typically have poor transparency so the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

More recently the use of so-called "occlusive" dressings for pressure sores and ulcers has gained acceptance. Most of these products are formed from several layers, including at least an inner skin-contacting layer and an outer backing layer. The dressing is applied as a cover for the sore or ulcer in a size providing a margin around the wound area that adhesively seals to the skin. An inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

The chemistry of acetoacetate compounds, and the Michael addition to acrylates has been described. For example, Mozner and Rheinberger reported the Michael addition of acetoacetates having a β-dicarbonyl group to triacrylates and tetracrylates to form gel products. See Macromolecular Rapid Communications 16 135-138 (1995).

U.S. Pat. No. 6,025,410 notes that the stoichiometry of the Michael donor to the Michael acceptor is critical to controlling the molecular weight. The reference teaches that certain soluble liquid uncrosslinked oligomers, made by one step Michael addition of acetoacetates to multi-acrylates, can be further crosslinked using ultraviolet light without using photoinitiators. If proportions below the claimed ranges are used, crosslinked gels or solid products are made which are not useful because only un-gelled, uncrosslinked liquid oligomers will further crosslink without adding photoinitiators. The described liquid oligomer compositions, since they are liquids, can readily be applied to various substrates using conventional coating techniques such as roll or spray prior to ultraviolet light cure.

U.S. Pat. No. 5,132,367 describes NCO-free resins and cured products thereof. The cured products are obtained by a Michael reaction of an acetoacetylated (meth)acrylic resin or an acetoacetylated polyester and an NCO-free polyurethane having at least two (meth)acrylic end groups. U.S. Pat. No. 5,132,367 however does not teach the use of these products in electrical applications.

EP 227454 discloses a process for preparing a cured polymer involving the Michael reaction of an acetoacetylated polyol and a poly α,β-unsaturated ester. The obtained cured products are said to exhibit excellent adhesion, excellent solvent resistance, excellent gloss retention, good flexibility and hardness.

U.S. Pat. No. 5,459,178 describes mixtures comprising an acetoacetate ester, an α,β-ethylenically unsaturated monomer and a liquid tertiary amine catalyst. A cured system is obtained by reacting these components. The acetoacetate ester used is prepared by transesterification of polyhydroxyl compound having an average of at least two hydroxy groups with an alkylacetoacetate.

U.S. Pat. No. 4,871,822 discloses a Michael reaction of olefinically unsaturated compounds with compounds containing at least two active hydrogen atoms for 2 component lacquers. As olefinically unsaturated compounds there are considered compounds having at least two α,β-unsaturated carbonyl groups. There are a large number of Michael donors including acetoacetylated polyols or polyamines and such compounds as e.g. acetylacetone or benzoylacetone.

David L. Trumbo in Polymer Bulletin 26, pages 265-270 (1991) discloses Michael addition polymers obtained from 1,4- and 1,3-benzenedimethanol diacetoacetates and tripropylene glycol diacrylate. The reference describes that in case the reactants are used in stoichometric amounts of the reactive groups, gelation of the system is observed. In another paper (Polymer Bulletin 26, pages 481-485 (1991)) the same author described Michael addition polymers obtained from the reaction of a bis(acetoacetyl) amide or an aliphatic acetoacetate and a di-acrylate comonomer. However, no utilisation or properties of the polymers are described in these articles.

WO 95/16749 describes a water-borne curable composition that comprises an acetoacetylated polymer in the form of an aqueous solution, dispersion or emulsion and a polyacrylate that has at least two (meth)acrylate end groups. According to this publication, such composition is stable even in the presence of a catalyst until the water is evaporated from the system.

The use of acetoacetyl chemistry, in particular the use of acetoacetylated resin, in thermosetting systems is further described in Journal of Coatings Technology Vol. 61 no. 771 page 31 to 37; Journal of Coatings Technology Vol. 65 no. 821 page 63 to 69; Surface Coatings Australia, September 1989 page 6 to 15; and Journal of Coatings Technology Vol. 61 no. 770 page 83 to 91.

U.S. Pat. No. 4,408,018 describes a method for effecting the cross linking of polymers comprises (a) introducing a plurality of pendant acetoacetate moieties into an acrylate polymer backbone; (b) mixing the polymer with (i) a crosslinking agent having at least two groups and (ii) a strong base catalyst effective to initiate a Michael reaction, and (c) effecting reaction between the pendant acetoacetate moieties and the polyacrylate. The polyacrylate containing pendant acetoacetate groups is made e.g. by copolymerising the acetoacetic ester of hydroxyethyl(meth)acrylate with the monomers forming the acrylate polymer. The polyacrylate cross linker is e.g. trimethylol propane triacrylate (I). The polyacrylate resin is esp. a styrene-acrylate copolymer contg. pendant acetoacetate gps.

SUMMARY OF THE INVENTION

Though there are known hydrophilic gel materials useful in medical applications such as wound dressings there is a need for materials that have the appropriate balance of absorption and cohesive strength. Further, it can be desirable to provide an occlusive material that is also transparent and/or flexible for use in a medical article such as a wound dressing or wound packing material. Yet further, it can be desirable to provide compositions that are melt-processible, and contain low residuals content.

The current invention describes reactive, melt-processible materials that may be cast on a web and cured by a step-growth addition to yield uniform coatings, particularly gel coatings. The polymers, crosslinking agent and extent of reaction, or crosslink density, can be varied in order to provide specific properties for a range of applications. The molecular weight of these materials is such that they can easily be processed, giving economic and/or environmental advantages. The materials can be subsequently cured to yield improved final mechanical properties. Thus, these materials represent a significant advance of the current art.

Briefly, the present invention provides novel hydrophilic, polymeric compositions prepared from a first component polymer containing pendent hydrophilic groups (preferably poly(alkylene oxide) groups, pendent Michael donor groups, and a co-reactive second component crosslinking agent having Michael acceptor functional groups and preferably a hydrophilic poly(alkylene oxide) segment.

In one aspect this invention provides a hydrophilic, crosslinkable, polymeric composition comprising:
  a) a first component polymer comprising a plurality of polymerized monomer units having pendent hydrophilic groups (preferably pendent poly(alkylene oxide) groups), and pendent Michael donor groups; and
  b) a crosslinking agent having Michael acceptor terminal groups, preferably a hydrophilic poly(alkylene oxide) having Michael acceptor terminal groups.

The present invention further provides a hydrophilic polymer that is the Michael reaction product of the first component polymer and the crosslinking agent. In the Michael reaction, certain enols, enolates, or equivalents add across the double bond of α,β-carbonyl compounds in an addition-elimination reaction.

This invention can have one or more of several advantages. The invention provides a hydrophilic, crosslinkable composition that produces no or minimal by-products, and that achieves its crosslink density by step-growth addition. In some embodiments, the composition is low in viscosity, readily melt processible and coatable, and has minimal residuals content such as solvents, monomers, plasticizers, by-products of condensation reactions or displacement reactions and/or viscosity modifiers. Unreacted monomers or low molecular weight species are potentially toxic or irritating, a particular concern in applications such as wound dressings, so in some embodiments the present compositions advantageously minimize such species.

In another aspect this invention provides a process for making a substrate bearing a coating of a crosslinked composition (such as a hydrophilic gel) on at least one surface thereof, comprising the steps of:
  a) combining the crosslinkable composition of the invention with a basic catalyst onto a substrate, and
  b) coating said composition, in the presence of a sufficient heat, to crosslink said composition.

For performance, environmental, and economic considerations, it is advantageous for some embodiments to create a composition having coatable viscosity of 10,000 centipoise or less (when measured at or below 100° C.), coat the composition on the substrate, then crosslink the components to build strength.

As used herein, the term "melt processible" or simply "processible" is used to refer to polymeric compositions that possess or achieve a suitable low viscosity for coating or extrusion at temperatures less than the decomposition temperature(s) of the polymers and crosslinking agent and less than the temperature at which premature gelation occurs, using conventional extrusion equipment without the need for addition of residuals such as solvents, monomers, plasticizers and/or viscosity modifiers and without the need for extraordinary pressures. Preferably the composition is melt processible at temperatures less than or equal to 100° C. Generally, the melt processible embodiments are those in which the first component polymer is oligomeric, i.e has a degree of polymerization of 300 or less.

In some embodiments, this invention provides absorbent medical articles and hydrophilic, polymeric gel materials for use therein, which are preferably transparent. The application of hydrophilic polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, medical applications encompass dental applications, including dental adhesives, restoratives, coatings, composites, sealants, etc. Because water swelling polymer gels have compositions and mechanical properties similar to those of biological tissues, such gels may be applied in a wide variety of fields in the future.

The ability to vary the crosslink density permits the modification of properties suitable for the various applications described previously. The novel compositions of the present invention cure to form crosslinked compositions possessing tailorable properties such as shear, peel, release, strength, hardness, elasticity, absorbancy and toughness, for example, through selection of the particular constituents, and by control of the crosslink density. While the requirements for medical gels and flexible coatings, for example, may be different, the structure of the material and density of linkages can be altered while still maintaining the same method of forming crosslinked compositions. The maximum crosslink density is predetermined by the percentage of Michael donor groups incorporated into the crosslinkable composition and the amount of crosslinking agent used. It may also be desirable to partially convert or cure a system for improved processing, while using a subsequent curing stage to obtain final properties.

By "gel" (or "polymer gel" or "polymeric gel material" or "hydrophilic gel") it is meant a gel material capable of swelling on contact with water-based fluids (such as body fluids including blood, plasma, and intracellular fluid or fluids similar to body fluids such as physiological saline), but does not dissolve in water. The gels are substantially continuous, i.e., lacking a cellular or void structure (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

By "absorbent" it is meant that the material is capable of absorbing fluids, particularly body fluids and preferably moderate to heavy amounts of body fluids, while retaining its structural integrity (i.e., remaining sufficiently intact such that it can perform the function of acting as a wound dressing, for example).

The term hydrophilic is used herein to describe polymer compositions, which are capable of absorbing water exposed thereto in significant quantity, typically more than about 50% by weight, preferably 100% by weight, more preferably more than 200% by weight.

Preferably the gel material is transparent and retains its transparency after absorption of fluids. By "transparent" it is meant that when the preferred material is applied to a patient (e.g., at a wound site), the area underlying the dressing can be visualized sufficiently to permit observation of the wound by a health care worker.

"acryl" is used in a generic sense and mean not only derivatives of acrylic acid, but also amine, thiol and alcohol derivatives, respectively;

"alkyl" and "alkylene" mean the monovalent and divalent residues remaining after removal of one and two hydrogen atoms, respectively, from a linear or branched chain hydrocarbon having 1 to 20 carbon atoms;

"lower alkyl" means $C_1$ to $C_4$ alkyl;

"aryl" and "arylene" mean the monovalent and divalent residues remaining after removal of one and two hydrogen atoms, respectively, from an aromatic compound (single ring and multi- and fused-rings) having 5 to 12 ring atoms and includes substituted aromatics such as lower alkaryl and aralkyl, lower alkoxy, N,N-di(lower alkyl)amino, nitro, cyano, halo, and lower alkyl carboxylic ester, wherein "lower" means $C_1$ to $C_4$.

"cycloalkyl" and "cycloalkylene" mean the monovalent and divalent residues remaining after removal of one and two hydrogen atoms, respectively, from a cyclic hydrocarbon having 3 to 12 carbon atoms;

"curable" means that a coatable material can be transformed into a solid, substantially non-flowing material by means of chemical cross linking.

"(meth)acryl" includes both acryl and methacryl groups.

"polyacryl" means a compound having two or more acryl groups that may function as Michael acceptors.

"crosslinking" means the formation of a polymeric network of infinite molecular weight and occurs in polymerizations with polymeric reactants having functionalities greater than two. Additional information may be found in G. Odian, *Principles of Polymerization*, 3rd edition, 1991, John Wiley & Sons: New York, p. 108. A crosslink is formed between the pendent polymerizable functional groups by a chain growth process.

Advantageously, the present invention provides crosslinkable compositions that are readily processed without appreciable residual content such as solvents, monomers, plasticizers and/or viscosity modifiers, and which do not contain byproducts from condensation or displacement reactions. Curable systems containing residual content can give rise to a significant increase in density when transformed from the uncured to the cured state causing a net shrinkage in volume. As is well known, shrinkage can cause a general loss of adhesion in many instances as well as significant movement and unpredictable registration. Shrinkage can also create residual stress in coatings, which can subsequently lead to mechanical failure.

In some embodiments, the composition of the present invention minimizes shrinkage due to solvent evaporation and/or monomer polymerization. The low shrinkage compositions of this invention are particularly useful in molding applications or in any applications where accurate molding and/or registration are required. The present invention provides a new class of crosslinkable polymers that may be formulated as 100% solids, melt processed, thermally cured and that exhibit properties that meet or exceed those of solvent-borne or syrup polymers (i.e. polymer compositions in which the polymer is dissolved in unreacted monomer). The present invention provides compositions that exhibit less than 2% shrinkage, and preferably less than 1%.

Further, the purity of the materials and clean environment for processing are also important to produce high performance materials. Polymers used for coatings and gels are often desirably delivered without significant amounts of volatile materials (such as monomeric species or other residuals) to eliminate any contamination, particularly at wound sites. However, the problems of residual volatile materials constitute a much more formidable challenge especially when acceptable limits of migratable, volatile impurities are on the order of a few parts per million. Industries such as medical and food packaging require materials of high purity and lower cost. In many embodiments, the present invention avoids problems due to residuals contamination, having a residuals content of less than 2 weight percent, preferably less than one weight percent.

DETAILED DESCRIPTION OF THE INVENTION

The present invention provides crosslinkable compositions useful in the preparation of hydrophilic gels. The compositions are prepared from polymers having pendent Michael donor groups and pendent hydrophilic groups, and are formed from ethylenically unsaturated monomers. The composition comprises:

a) a first component polymer comprising a plurality of polymerized monomer units having pendent hydrophilic groups, preferably poly(alkylene oxide) groups, and pendent Michael donor groups; and b) a crosslinking agent having Michael acceptor groups, and preferably comprises a hydrophilic poly(alkylene oxide) groups having-two or more terminal Michael accepter groups, such as acryl groups.

The composition comprises, per 100 parts by weight of a first component polymer, a sufficient amount of said crosslinking agent to provide greater than two crosslinks per first component polymer chain when cured or crosslinked. The relative amounts depending on the amounts of the two components and the amounts of Michael donor and Michael accepter equivalents in the polymer and crosslinker agent, respectively.

The relative amounts of said first component polymers and the crosslinking agent may vary widely; i.e. from 50 to 99.9 parts by weight, preferably 80 to 99.9 parts by weight, of the first component polymer and from 0.1 to 50 parts by weight of the crosslinking agent, preferably 0.1 to 20 parts by weight. Generally the amount of said crosslinking agent is ten parts by weight or less. However, the relative amounts are chosen so that the crosslinked composition is hydrophilic, i.e. absorbs at least 50 wt. % water.

In one embodiment the first component polymer (a) comprises:
- a) from 25 to 75 parts by weight of polymerized monomer units having pendent, hydrophilic groups, preferably poly(alkylene oxide) groups,
- b) from 25 to 75 parts by weight of polymerized monomer units derived from of an ethylenically-unsaturated monomer having a pendent Michael donor groups;
- c) from 0 to 25 parts by weight of polymerized monomer units derived from acrylic acid esters, preferably of nontertiary alkyl alcohols containing 1-14 carbon atoms; and
- d) from 0 to 10 parts by weight of at least one other monomer.

The first component polymer comprises monomers having a hydrophilic group, i.e. "hydrophilic monomers". As used herein "hydrophilic monomers" are those polymerizable monomers having a water miscibility (water in monomer) of at least 1 wt. %, preferably at least 5 weight % without reaching a cloud point and are inclusive of poly(alkylene oxide) monomers. The polymer may comprise 25 to 75 parts by weight of such monomer units. Preferably the polymer generally comprises 50 parts by weight or less, of such monomer units.

Hydrophilic monomers are used to increase the hydrophilicity, absorbency and/or improve the mechanical properties (e.g. the tensile strength) of the crosslinked polymer used in forming the gel material. Hydrophilic monomers can also provide compliance to the resultant polymer. Examples of suitable hydrophilic monomers include 2-hydroxyethyl (meth)acrylate (HEMA), 2-hydroxypropyl(meth)acrylate, 3-hydroxypropyl(meth)acrylate, 2, 3-dihydroxypropyl (meth)acrylate, 4-hydroxybutyl(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, (meth)acrylic acid, itaconic acid, beta-carboxyethyl acrylate, glycerol methacrylate, [2-(meth)(acryloyloxy)ethyl]trimethylammonium chloride, [2-(meth)(acryloyloxy)ethyl]trimethylammonium methyl sulfate, and combinations thereof. Preferred polar monomers include 2-hydroxyethyl(meth)acrylate (HEMA), N-vinyl pyrrolidone, N-vinyl acetamide, dimethylarcrylamide, and mixtures thereof, and the like. Preferably the hydrophilic monomer has a pendent poly(alkylene oxide) group.

The first component polymer preferably comprises polymerized monomer units derived from of an ethylenically-unsaturated monomer having pendent poly(alkylene oxide) group of the formula:

$$Z\text{-}Q\text{-}(CH(R^1)\text{---}CH_2\text{---}O)_n\text{---}R^2, \tag{I}$$

wherein Z is a polymerizable ethylenically unsaturated moiety, $R^1$ is a H or a $C_1$ to $C_4$ alkyl group, $R^2$ is a H, a $C_1$ to $C_4$ alkyl group, aryl group, or combinations thereof and n is from 2 to 100, preferably 5 to 20, Q is a divalent linking group selected from alkylene, —O—, —$NR^1$—, —S—, and combinations thereof, The polymer comprises from 25 to 75 parts by weight, preferably 50 parts by weight or less, of such monomer units. Preferably, Z— represents an (meth)acryl group.

In one embodiment, the poly(alkylene oxide) group is a poly(ethylene oxide) (co)polymer. In another embodiment, the pendent poly(alkylene oxide) group is a poly(ethylene oxide-co-propylene oxide) copolymer. Such copolymers may be block copolymers, random copolymers, or gradient copolymers.

The monomer having a poly(alkylene oxide) group can be prepared, for example, by reacting mono- or di-functional alkylene oxide (co)polymers (which are typically commercially available) with reactive ethylenically unsaturated compounds (e.g., (meth)acryl compounds). The functional groups terminating the poly(alkylene oxide) may include hydroxy groups, amine groups, lower alkyl ether groups, aryl ether groups and carboxy groups.

A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. Preferably, the monomer is prepared by reacting the mono- or di-functional alkylene oxide (co)polymer with (meth)acrylic anhydride. Typically, if a stoichiometric amount of the ethylenically unsaturated reactant is combined with the monofunctional alkylene oxide (co)polymer (such as a monohydroxy terminated alkylene oxide (co)polymer), 100% conversion to the monosubstituted product is obtained.

Examples of suitable monofunctional poly(alkylene oxide) monomers include poly(ethylene oxide) (meth)acrylate, poly(propylene oxide) (meth)acrylate, poly(ethylene oxide-propylene oxide) (meth)acrylate, and combinations thereof. Such monomers preferably include one nonreactive end group such as ($C_1$-$C_4$)alkoxy, aryloxy (e.g., phenoxy), and ($C_1$-$C_4$)alkaryloxy. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

The first component polymer comprises polymerized monomer units derived from an ethylenically-unsaturated monomer having pendent Michael donor groups of the formula:

$$W^1\text{---}CHR^4\text{---}C(O)\text{-}Q\text{-}Z \tag{II}$$

or $$W^1\text{---}NH\text{---}C(O)\text{-}Q\text{-}Z \tag{III}$$

wherein
$R^4$ represents hydrogen, an alkyl group or an aryl group;
$W^1$ is selected from a cyano group, a nitro group, an alkyl carbonyl group, an alkoxy carbonyl group, an aryl carbonyl group, an aryloxy carbonyl group, an amido group, and a sulphonyl group,
Z is a polymerizable ethylenically unsaturated moiety, and
Q is a divalent linking group selected from alkylene, —O—, —$NR^1$—, —S—, and combinations thereof (such as oxyalkylene), wherein $R^1$ is a H or a $C_1$ to $C_4$ alkyl group.

With respect to Formulas I, II and III, Z-Q represents an ethylenically unsaturated polymerizable group which may include:

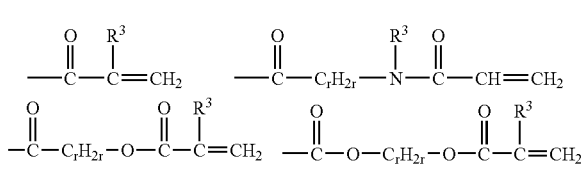

-continued

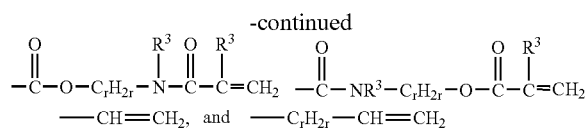

wherein R³ is H or Me and r = 1–10.

Useful Michael donor monomers include 2-acetoacetoxyethyl methacrylate, and allyl acetoacetate. The first component polymer generally comprises 25 to 75 parts by weight of polymerized monomer units derived from of an ethylenically-unsaturated monomer having pendent Michael donor groups.

With respect to both component monomers (those having pendent poly(alkylene oxide) groups and those having pendent Michael donor groups), it will be understood, with respect to the above description, that the pendent groups may be incorporated into the first component polymer in at least two ways: the "direct method" whereby a monomer unit having the pendent group (either the poly(alkylene oxide) groups or the Michael donor groups) is polymerized with the other component monomers to produce the first component polymer, or the "indirect method" whereby the polymer is provided with reactive functional groups, which are subsequently functionalized with Michael donor compounds having a co-reactive functional group to produce the first component polymer.

Using the "direct method" of incorporating the pendent Michael donor group, useful monomers include those having Michael donor groups and a functional group capable of free radical addition such as those groups containing a carbon-carbon double bond (as defined for Formulas I, II and III supra), including vinyl, vinyloxy, (meth)acrylic, (meth)acrylamido, and acetylenic functional groups. The preferred "direct method" of incorporating the pendent hydrophilic groups (such as the poly(alkylene oxide) groups) uses monomers comprising a functional group capable of free radical addition such as those groups containing a carbon-carbon double bond and a hydrophilic group.

An indirect method of incorporating the pendent groups into the polymer is to include among the monomer units of the polymer some that comprise a reactive functional group. Useful reactive functional groups include, but are not limited to, hydroxyl, amino, oxazolonyl, oxazolinyl, acetoacetyl, azlactonyl, carboxyl, isocyanato, epoxy, aziridinyl, acyl halide, and cyclic anhydride groups. Preferred among these are carboxyl, hydroxyl, amino, azlactonyl and aziridinyl groups. These pendent reactive functional groups are reacted with compounds having hydrophilic groups and/or a Michael donor group and a functional group that is co-reactive with the reactive pendent functional group. When the two functional groups react, a polymer with the requisite pendent group results. In some applications, it may be desirable to use less than a stoichiometric equivalent of compounds that comprise co-reactive functional groups, so that some of the pendent functional groups on the polymer(s) remain unreacted.

Using the "indirect method" of incorporating the pendent, Michael donor groups, useful reactive functional groups include hydroxyl, secondary amino, oxazolinyl, oxazolonyl, acetyl, acetonyl, carboxyl, isocyanato, epoxy, aziridinyl, acyl halide, vinyloxy, and cyclic anhydride groups. Where the pendent reactive functional group is an isocyanato functional group, the co-reactive functional group preferably comprises a secondary amino or hydroxyl group. Where the pendent reactive functional group comprises a hydroxyl group, the co-reactive functional group preferably comprises a carboxyl, ester, acyl halide, isocyanato, epoxy, anhydride, azlactonyl or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophile and electrophic functional groups.

In a preferred method, pendent acetoacetate groups may be incorporated into the first component polymer in an indirect method by which the first component polymer has pendent nucleophilic functional groups such as hydroxyl or amine functional groups. These may be subsequently reacted with diketene or t-butylacetoacetate to provide the requisite pendent acetoacetate groups.

Representative examples of useful monomers having reactive functional groups include hydroxyalkyl(meth)acrylates such as 2-hydroxyethyl(meth)acrylate, 3-hydroxypropyl (meth)acrylate, 2,3-dihydroxypropyl (meth)acrylate, 4-hydroxybutyl(meth)acrylate and 2-(2-hydroxyethoxy)ethyl (meth)acrylate; aminoalkyl(meth)acrylates such as 3-aminopropyl (meth)acrylate and 4-aminostyrene; oxazolinyl compounds such as 2-ethenyl-1,3-oxazolin-5-one, 2-vinyl-4,4-dimethyl-1,3-oxazolin-5-one, 2-isopropenyl-4,4-dimethyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl(meth)acrylate; epoxy-substituted compounds such as glycidyl(meth)acrylate; aziridinyl-substituted compounds such as N-acryloylaziridine and 1-(2-propenyl)-aziridine; and acryloyl halides such as (meth)acryloyl chloride.

The first component polymer may further comprise alkyl (meth)acrylate esters. Alkyl(meth)acrylate ester monomers useful in the invention include straight-chain, cyclic, and branched-chain isomers of alkyl esters containing $C_1$-$C_{30}$ alkyl groups. Due to $T_g$ and sidechain crystallinity considerations, preferred alkyl acrylate esters are those having from $C_5$-$C_{12}$ alkyl groups, although use of $C_1$-$C_4$ and $C_{13}$-$C_{14}$ alkyl groups are also useful if the combinations provide a molecule with an average number of carbon atoms between $C_5$ and $C_{12}$. However, for many applications higher, i.e. $C_{12}$-$C_{30}$ alkyl groups may be preferred. Useful specific examples of alkyl acrylate esters include: methyl acrylate, ethyl acrylate, n-propyl acrylate, 2-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, tridecyl acrylate, and tetradecyl acrylate. The corresponding (meth)acrylamide and thio esters may also be used. The polymer may comprise 0 to 25 parts by weight of such monomer units. Where present, the polymer generally comprises less than 25 parts by weight.

The first component polymers may further comprise other monomers, not previously described. The selection of the "other monomers" useful in preparing the polymer(s) is such that the ultimate crosslinked material has properties suitable for its application. For example, "other monomers" may be used to increase the tensile strength or other mechanical properties, or to control the $T_g$ of the polymer. Representative examples of "other monomers" include free-radically polymerizable monomers having at least one ethylenically unsaturated polymerizable group that are copolymerizable with the aforementioned monomers, and include vinyl monomers such as vinyl acetate, styrenes, allyl ethers, maleic anhydride, and alkyl vinyl ethers. Other monomers generally comprising less than 10 parts by weight, e.g. 0 to 10 parts by weight of the first component polymer.

The polymers used in forming the hydrophilic, crosslinkable composition of the present invention can be produced by polymerizing the above-described monomers by conventional polymerization methods. Typical polymerization methods that can be used include thermal and/or photochemical as well as bulk and solution polymerization.

The first component polymer may be prepared (e.g., by solution polymerization followed by isolation). Any residual monomer and/or solvents used in the preparation are generally removed by conventional techniques such as distillation, vacuum evaporation, etc., to reduce the residual content to less than 2 wt. %, prior to crosslinking. The polymerizations may be conducted in the presence of suitable solvents such as ethyl acetate, toluene and tetrahydrofuran that are unreactive with the functional groups of the components of the first and second components.

In a typical solution polymerization method, a monomer mixture is heated with stirring in the presence of a solvent and a polymerization initiator. Examples of the solvent are methanol, tetrahydrofuran, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, 2-(1-cyano-1,3-dimethyl-butylazo)-2,4-dimethyl-pentanenitrile and 2,2'-azo-bis-isobutyronitrile. Those polymerization initiators can be used alone or as mixtures thereof.

In a typical photopolymerization method, a monomer mixture may be irradiated with ultraviolet (UV) rays in the presence of a photopolymerization initiator (i.e., photoinitiators). Preferred photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-rimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenylpropan-1-one (DAROCUR 1173). Particularly preferred photoinitiators are IRGACURE 819, 184 and 2959.

These photo- and thermal initiators can be employed in concentrations ranging from about 0.0001 to about 3.0 pbw, preferably from about 0.001 to about 1.0 pbw, and more preferably from about 0.005 to about 0.5 pbw, per 100 pbw of the monomer composition.

The molecular weight, $M_w$, of the first component polymer is generally less than 100,000, typically less than 50,000. In some embodiments, such as where melt-processible compositions are desired, the first component polymer is oligomeric, i.e. has a degree of polymerization of 300 or less.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art. Useful chain transfer agents also include cobalt chelates, as described in U.S. Pat. Nos. 4,680,352 and 4,694,054, and polymeric chain transfer agents as described in U.S. Pat. Nos. 5,362,826 and 5,773,534.

Where the first component polymer is an oligomer, the oligomers have an average degree of polymerization (DP) generally less than about 300. The greater increase in viscosity (for polymers having a degree of polymerization greater than 300), is attributed to entanglements of polymer chains. It has been shown empirically that polymers or oligomers with less than 300 repeat units are not entangled. If desired, higher molecular weight polymers may be blended with lower molecular weight oligomers so that the mixture has a viscosity of 500 to 10,000 cPs at temperatures less than 100° C.

First component polymers have relatively low molecular weight, then build molecular weight (and strength) by a chain-growth process of the polymers and crosslinking agent, through the polymerizable functional groups. As result of the relatively low molecular weight, the polymers are easily processible in operations such as coating, spraying, extrusion and molding, because of the low melt viscosity prior to crosslinking, and without the need for residuals, such as solvents, plasticizers or viscosity modifiers. With the present oligomers, the slope of the log-log plot of viscosity vs. molecular weight ($M_n$) is about 1, whereas for higher molecular weight polymers the slope is 3.4. The polymers of the present invention provide processibility, and then crosslinking of the oligomers provides the needed physical properties such as toughness, hardness, tensile strength and others that are manifested in the cured state. Unless otherwise indicated molecular weight will refer to number average molecular weight.

Liquid polymers may be obtained if the glass transition temperature of the polymer component is below ambient temperature and the molecular weight of the polymer component is below entanglement molecular weight (i.e. a degree of polymerization of less than about 300). Low melting solids may be obtained when the $T_g$ is at or below ambient temperature. Powders may be obtained when the $T_g$ is above ambient temperature. Due to the amount of poly(alkylene oxide), the polymers are generally low melting solids or liquids.

In addition to the first component polymer, the curable composition of the invention further comprises a crosslinking agent having Michael acceptor groups, and preferably comprises a hydrophilic poly(alkylene oxide) groups having two or more terminal acryl groups.

Useful polyacryl compounds include those of the general formula:

$$R^5\text{—}(Q\text{-}C(O)\text{—}CH\text{=}CH_2)_z \qquad (IV)$$

wherein each Q is selected from alkylene, —O—, —$NR^1$—, or —S— or combinations thereof where each $R^1$ independently represents H, an alkyl group having from 1 to 4 carbon atoms;

Each $R^5$ independently represents a polyvalent organic group having a valence of z, which can be cyclic, branched, or linear, aliphatic, aromatic, or heterocyclic, having carbon, hydrogen, nitrogen, nonperoxidic oxygen, sulfur, or phosphorus atoms; preferably $R^5$ represents a hydrophilic poly (alkylene oxide) group;

each z independently represents an integer greater than or equal to 2. Preferably, z has a value of 2-6 (more preferably z has a value of 2-5, most preferably 2, or where a mixture of polyacrylates are used, z has an average value of about 2).

In one embodiment, $R^5$ may be a polyvalent organic group having a valence of at least 3. Examples of polyvalent groups $R^5$ include butylene; ethylene; propylene; and 4-oxaheptalene; hexylene; and 1,4-bis(methyl)cyclohexylene. All isomers or the alkylene groups are envisioned, such a 1,2-, 1,3- and 1,4-butylene isomers.

Useful polyacryl compounds include, for example, acrylate monomers selected from the group consisting of (a) diacryl containing compounds such as ethylene glycol diacrylate, 1,3-butylene glycol diacrylate, 1,4-butanediol diacrylate, 1,6-hexanediol diacrylate, cyclohexane dimethanol diacrylate, alkoxylated hexanediol diacrylate, neopentyl glycol diacrylate, caprolactone modified neopentylglycol hydroxypivalate diacrylate, cyclohexanedimethanol diacrylate, diethylene glycol diacrylate, dipropylene glycol diacrylate, bisphenol-A diacrylate, ethoxylated bisphenol-A diacrylate, hydroxypivalaldehyde modified trimethylolpropane diacrylate, neopentyl glycol diacrylate, polyethylene glycol diacrylate, propoxylated neopentyl glycol diacrylate, tetraethylene glycol diacrylate, tricyclodecanedimethanol diacrylate, triethylene glycol diacrylate, tripropylene glycol diacrylate; (b) triacryl containing compounds such as glycerol triacrylate, ethoxylated triacrylates (e.g., ethoxylated trimethylolpropane triacrylate, pentaerythritol triacrylate, propoxylated triacrylates (e.g., propoxylated glyceryl triacrylate, propoxylated trimethylolpropane triacrylate, tris(2-hydroxyethyl)isocyanurate triacrylate; (c) higher functionality acryl-containing compounds such as ditrimethylolpropane tetraacrylate, dipentaerythritol pentaacrylate, ethoxylated pentaerythritol tetraacrylate, pentaerythritol tetraacrylate, caprolactone modified dipentaerythritol hexaacrylate; (d) oligomeric acryl compounds such as, for example, urethane acrylates, polyester acrylates, epoxy acrylates; polyacrylamide analogues of the foregoing; and combinations thereof.

Such compounds available from vendors such as, for example, Sartomer Company, Exton, Pa.; UCB Chemicals Corporation, Smyrna, Ga.; and Aldrich Chemical Company, Milwaukee, Wis. Additional useful acrylate materials include hydantoin moiety-containing polyacrylates, for example, as described in U.S. Pat. No. 4,262,072 (Wendling et al.).

Other useful polyacryl compounds also include, for example, free-radically polymerizable acrylate oligomers and polymers having pendant (meth)acryl groups wherein at least two of the (meth)acryl groups are acryl groups. There is a differential reactivity between acryl and methacryl groups with respect to Michael-type addition. Michael-type addition typically occurs easily with acryl groups, but may occur only with difficulty if at all, in the case of methacryl groups. For this reason, the polyacryl component typically has at least two acryl group (e.g., as part of acryloxy or acrylamido functionality), although the poly(meth)acryl compound may also have additional (meth)acryl groups (e.g., as part of methacrylate or methacrylamido functionality). Advantageously, composition may be prepared in which Michael addition occurs through the acryl groups, leaving methacryl groups unreacted. Such unreacted methacryl groups may be subsequently free-radically polymerized.

With respect to the useful polyacryl compounds presented above, it will be understood that the corresponding amides or thioesters are also useful. The multifunctional ethylenically unsaturated monomer is preferably an ester of acrylic acid. It is more preferably selected from the group consisting of a difunctional ethylenically unsaturated ester of acrylic, a trifunctional ethylenically unsaturated ester of acrylic, a tetrafunctional ethylenically unsaturated ester of acrylic, and a combination thereof. Of these, difunctional and trifunctional ethylenically unsaturated esters of acrylic acid are more preferred.

Other useful acrylate oligomers include acrylated epoxies, for example, diacrylated esters of epoxy-functional materials (e.g., diacrylated esters of bisphenol A epoxy-functional material) and acrylated urethanes. Useful acrylated epoxies include, for example, acrylated epoxies available under the trade designations "EBECRYL 3500", "EBECRYL 3600", "EBECRYL 3700", and "EBECRYL 3720" from UCB Chemicals Corporation. Useful acrylated urethanes include, for example, acrylated urethanes available under the trade designations "EBECRYL 270", "EBECRYL 1290", "EBECRYL 8301", and "EBECRYL 8804" from UCB Chemicals Corporation.

Where a hydrophilic polymer is desired, a polyacryl poly (alkylene oxide) may be used. The functional groups terminating the poly(alkylene oxide) may include hydroxy groups, and amine groups, which may be acrylated. Poly(ethylene oxide), poly(propylene oxide), poly(ethylene oxide-propylene oxide), and combinations thereof may be acrylated at one or both terminal ends. A useful hydrophilic polyacryl crosslinking agent is of the formula:

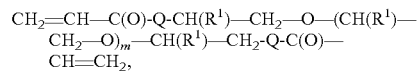
$$CH_2=CH-C(O)-Q-CH(R^1)-CH_2-O-(CH(R^1)-CH_2-O)_m-CH(R^1)-CH_2-Q-C(O)-CH=CH_2,$$

wherein $R^1$ is a H or a $C_1$ to $C_4$ alkyl group, and m is from 1 to 500, and Q is a divalent linking group selected from alkylene, —O—, —$NR^1$—, —S—and combinations thereof The crosslinking agent having a poly(alkylene oxide) group can be prepared, for example, by reacting di-functional alkylene oxide (co)polymers (which are typically commercially available) with reactive ethylenically unsaturated compounds (e.g., acrylates). The functional groups terminating the poly(alkylene oxide) may include hydroxy groups, amine groups and carboxy groups. A variety of reactive ethylenically unsaturated compounds such as acryl compounds can be used including, but not limited to, acrylic acid, acryloyl chloride, acrylic anhydride, and 2-isocyanatoethyl acrylate.

Preferably, the crosslinking is prepared by reacting the di-functional alkylene oxide (co)polymer with alkyl acrylates. Typically, if a stoichiometric amount of the ethylenically unsaturated reactant is combined with the difunctional alkylene oxide (co)polymer (such as a hydroxy terminated alkylene oxide (co)polymer), 100% conversion to the disubstituted product is obtained.

Examples of suitable difunctional poly(alkylene oxide) crosslinking agents include poly(ethylene oxide) diacrylate, poly(propylene oxide) diacrylate, poly(ethylene oxide-propylene oxide) diacrylate, and combinations thereof. Such copolymers may be block copolymers, random copolymers, or gradient copolymers. These monomers can be of a wide range of molecular weights and are commercially available from sources such as Sartomer Company, Exton, Pa.; Shin-nakamura Chemical Co., Ltd., Tokyo, Japan; Aldrich, Milwaukee, Wis.; and Osaka Organic Chemical Ind., Ltd., Osaka, Japan.

Useful acrylated polyether oligomers include polyethylene glycol diacrylates available, for example, under the trade designations "SR259" and "SR344" from Sartomer Company. Acrylated polyester oligomers are available, for example, under the trade designations "EBECRYL 657" and "EBECRYL 830" from UCB Chemicals Corporation.

As previously described, the composition of the present invention comprises a first polymer component with a plurality of pendent groups (i.e. pendent poly(alkylene oxide and Michael donor groups), and a second crosslinking component with a plurality of Michael acceptor groups and preferably a hydrophilic poly(alkylene oxide) group. The amount of each component monomers and the relative amounts of the first component polymer and crosslinking agent may be adjusted to obtain compositions having desired hydrophilicity, melt-processibility and mechanical properties.

The stoichiometry of the reactants is based not on molar amounts of the components, but molar functional group equivalents. For example, a pendent acetoacetate group has two protons alpha to both of the carbonyl groups, and so can react with two Michael acceptor acryl groups. Thus acetoacetate has two functional group equivalents. In general, the molar ratio of Michael donor functional group equivalents of the first component polymer ("donor equivalents") is equal to Michael acceptor functional group equivalents of the crosslinking agent ("acceptor equivalents"), is less than 5:1, more preferably less than 1.5:1 and most preferably less than 1.1:1.

As some compositions may have an excess of donor equivalents to acceptor equivalents, all or part of the excess donor equivalents may be reacted with a Michael acceptor groups of a monoacryl compound. Preferably the ratio of Michael donor functional group equivalents of the first component polymer ("donor equivalents") is approximately equal to Michael acceptor functional group equivalents of the crosslinking agent and monoacryl compounds ("acceptor equivalents") plus added monoacryl compounds. Useful ranges of donor equivalent to total acceptor equivalent (from the crosslinking agent and the monoacryl compound) is 1.2:1 to 1:1.2. More preferably, the Michael donors equivalent are in excess of the total Michael acceptor equivalent, or about 1.2:1 to 1:1. Excess monoacryl compounds may be removed by vacuum evaporation to minimize the amount of residuals in the composition.

Useful monoacryl compounds include those alkyl acrylate esters and thioesters, hydrophilic monomers, functional monomers and other monomer described supra with respect to the first component polymer. It will be understood with respect to that description, that the monoacryl component must be a Michael acceptor; that acryl compounds are useful while the corresponding methacryl are generally unreactive in a Michael reaction.

The monoacryl monomer may be used to regulate and control the degree of crosslinking and to provide a Michael addition polymer having pendent reactive functional groups (where the monoacryl component is a functional monoacryl compound such as hydroxyethyl acrylate). Useful functional monoacryl compounds include those acryl compounds that undergo a Michael addition and further include a functional group capable of further reaction, such as a hydroxyl, amino, azlactone, oxazolinyl, 3-oxobutanoyl (i.e., acetoacetyl), carboxyl, isocyanato, epoxy, aziridinyl, acyl halide, vinyloxy, or cyclic anhydride group.

The present invention further provides a process for preparing a hydrophilic, crosslinked polymer comprising the steps of 1) providing a first component polymer, 2) crosslinking the polymer with a crosslinking agent having at least two Michael acceptor groups, and 3) optionally reacting all or a portion of unreacted Michael donor groups of the first component polymer with a monoacryl component. Steps 2 and 3 may be concurrent. Optionally a portion of the Michael donor groups may be reacted a monoacryl component prior to crosslinking.

A coatable polymer composition may be prepared by combining the first polymer component, the crosslinking agent and a basic catalyst. Partial conversion of the two components may be desirable to achieve a thickened solution exhibiting a coatable viscosity of from about 500-10,000 cPs at 22° C., more preferably from about 750 to 7500 cPs.

A suitable catalyst for the Michael reaction is a base of which the conjugated acid preferably has a pKa between 12 and 14. Most preferably used bases are organic. Examples of such bases are 1,4-dihydropyridines, methyl diphenylphosphane, methyl di-p-tolylphosphane, 2-allyl-N-alkyl imidazolines, tetra-t-butylammonium hydroxide, DBU (1,8-diazabicyclo[5.4.0]undec-7-ene) and DBN (1,5-diazabicyclo[4.3.0]non-5-ene), potassium methoxide, sodium methoxide, sodium hydroxide, and the like. A preferred catalyst in connection with this invention is DBU and tetramethylguanidine. The amount of catalyst used in a curable composition in accordance with the present invention is preferably between 0.05% by weight and 2% by weight more preferably between 0.1% by weight and 1.0% by weight.

Preferably, a curable composition in connection with the present invention is prepared by mixing two parts together. One part contains the catalyst and the other contains the reactants, i.e. the polymer component, and the crosslinking agent (i.e. polyacryl component). Although it is also possible to have the catalyst together with one of the reactants in one part and having the other reactant in the other part, these embodiments generally produce inferior results, presumably because reaction of the catalyst with the reactant can take place. The extent of this reaction will generally depend on the kind of catalyst and reactants used.

If so desired, measuring the refractive index of the composition material especially in bulk can be used to monitor the extent of polymerization. The refractive index changes linearly with respect to conversion. This monitoring method is commonly applied in polymerization kinetics work. See discussions about the method in, for example, G. P. Gladyshev and K. M. Gibov, *Polymerization at Advanced Degrees of Conversion,* Keter Press, Jerusalem (1970).

The crosslinked composition can be characterized as a polymer having polymer chains crosslinked with at least one hydrophilic poly(alkylene oxide) moiety. Thus, during exposure to the basic catalyst, the Michael donor group of the polymer adds to the Michael accepter group of the crosslinking agent to form a crosslink between the polymer chains and crosslinking agent. In general, the present crosslinked composition has effective molecular weight between crosslinks, ($M_c$), of greater than or equal to 1,000 and preferably greater than 3,000. Effective molecular weight between crosslinks ($M_c$), may be measured by dynamic mechanical analysis.

The degree of crosslinking may be easily controlled by the number and concentration of pendent Michael donor groups that are pendent on the polymer(s) and the number and concentration of pendent Michael accepter groups of the crosslinking agent. Generally the smaller the $M_c$, the lower the elasticity and hence harder the crosslinked composition.

Curable compositions according to the present invention may be coated on a substrate and at least partially cured to provide a composite article. Suitable substrates include, for example, glass (e.g., windows and optical elements such as, for example, lenses and mirrors), ceramic (e.g., ceramic tile), cement, stone, painted surfaces (e.g., automobile body panels, boat surfaces), metal (e.g., architectural columns), paper (e.g., adhesive release liners), cardboard (e.g., food containers), thermosets, thermoplastics (e.g., polycarbonate, acrylics, polyolefins, polyurethanes, polyesters, polyamides, polyimides, phenolic resins, cellulose diacetate, cellulose triacetate, polystyrene, and styrene-acrylonitrile copolymers), and combinations thereof. The substrate may be a film, sheet, or it may have some other form.

The curable composition may be applied to the substrate by conventional techniques such as, for example, spraying, knife coating, notch coating, reverse roll coating, gravure coating, dip coating, bar coating, flood coating, or spin coating. Typically, the curable composition is applied to the substrate resulting in a dried cured layer having a thickness in a range of from about 25 micrometers to about 1000 micrometers, although thinner and thicker layers may also be used. Next, any optional solvent is typically at least partially removed (e.g., using a forced air oven), and the curable composition is then at least partially cured to form a coating, for example, as described hereinabove.

When the composition of the invention is used to prepare hydrophilic gel materials for medical applications, the gel can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocaine, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product of this invention is cured as long as they do not interfere with polymerization of the polymer. Preferably, they are added in an amount or manner that does not interfere with the function or clarity of the finished gel material.

Optionally, the gel material of the present invention can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. The gel material of the present invention preferably includes an amount of the hydrocolloid such that the material is transparent (preferably, the total light transmittance is greater than 84% per ASTM D1003-00). Typically, the amount of hydrocolloid, if used, is less than about 5 wt-%, based on the total weight of the gel material.

Other additives that can be incorporated into the gel material of the present invention include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate, and alpha-methylstyrene, the latter of which can also be a hydrophobic monomer as discussed above); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the gel material of the present invention is substantially free of residuals, including water. This is advantageous at least because special packaging is not required. Furthermore, residuals can migrate to other parts of a dressing, for example, which can be detrimental to the integrity of the dressing, or into the body of the patient on which the dressing is disposed.

Optionally, the gel material may have a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e. expansion of the gel layer through a porous film) and further avoids premature separation of an adhesive layer from the skin.

The optional pattern imparted to the surface of a layer of the gel material may be any suitable preselected three-dimensional pattern. Preferably, the pattern is one that increases the surface area available for absorption and reduces swelling into the wound, retards mushrooming, and/or enhances integrity of the material upon hydration. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element is advantageously chosen to present minimal surface area in contact with a wound or the facing film if present. The minimal surface area further retards the tendency of the gel material to swell into the wound, mushroom, or adhere to the wound site. Especially useful elements include pyramids, cones and truncated versions thereof, and ridges that are triangular in cross section. The elements may be random or non-random in the x direction, the y direction, or both. For ease of manufacture, it is preferable that the pattern comprises a non-random array of elements disposed on the surface of the gel.

If desired, a pattern may also be imparted to the outer face of the gel layer (i.e., the major surface of the gel layer that faces away from the wound surface). Imparting such a pattern increases the surface area of the gel layer and may promote greater evaporation of the fluid from the gel material. The pattern may be the same or different from the pattern on the facing surface of the gel material, as can the size of the pattern elements. Further, the individual elements on either surface of the gel material may be protuberances extending form the surface, or may be depressions in the surface.

An optional patterned surface may be imparted to the gel material by conventional molding techniques. Alternatively, a desired pattern may be imparted using an embossing technique. Examples of such techniques are described in U.S. Pat. No. 6,566,575, (Stickels et al.), incorporated herein by reference.

If desired, the gel material may be in direct contact with the wound and/or skin surface. However, direct contact may be provided by other suitable hydrocolloid and hydrogel absorbent materials as well.

In a preferred medical article, the gel material forms a layer that is generally about 25 micrometers (i.e., microns) to about 1000 micrometers in total thickness.

Optionally, a wound dressing of the invention may include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described above prepared from the polymeric composition. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer.

Generally, the second absorbent layer functions as a "barrier" between the first absorbent layer (which may partially "disintegrate" when exudate is unevenly, rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 200 percent of its weight after immersion in an isotonic saline solution after 24 hours at room temperature.

A typical wound dressing of the present invention preferably includes a porous or non-porous facing layer to provide a fluid permeable barrier between the wound site and the gel layer. The facing layer allows transport of moisture (i.e. fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate (MVTR) of at least 300 grams per square meter per 24 hours at 80% relative humidity differential at 40° C. (per method of U.S. Pat. No. 5,733,570 (Chen et al.)), is impermeable to liquid water throughout substantially its entire imperforate area and contains perforations for passing wound exudate through the facing layer. This means that the facing layer does not pass liquid water under normal wound treatment conditions except at the places in the facing layer that are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyetheramide, polyurethanes, chlorinated polyethylene, styrenetbutadiene block copolymers (KRATON brand thermoplastic rubber, Shell Chemical Company, Houston, Tex.) and poly (vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the gel layer, into which the exudate from the wound passes. This reservoir does not permit liquid water or exudate to pass out of it. Instead, the gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 micrometers to about 50 micrometers in thickness, preferably about 12 micrometers to about 25 micrometers. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes such as those available under the trade designation ESTANE from B.F. Goodrich, Cleveland, Ohio, elastomeric polyester such as those available under the trade designation HYTREL from E.I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 $g/m^2/24$ hrs, preferably about 3000 to 4000 $g/m^2/24$ hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in U.S. Pat. No. 6,420,622 (Johnston et al.).

Many different constructions of a wound dressing are possible with the facing layer, the gel layer, and the backing layer. In one embodiment, the areas of the facing layer and the backing layer are greater than that of the gel layer and the facing layer is bonded to the backing layer, thereby forming a pouch, with the gel disposed between the two. In another embodiment, one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area than the gel layer. Alternatively, the backing and facing layers may be bonded to each other, and may or may not be bonded to the gel layer. In these last constructions, the gel layer is constrained within a pouch created by the attachment of the facing and backing layers to each other. The layers may be bonded to each other by any conventional means such as adhesives, heat-sealing, or other bonding means.

It is preferred that the facing and backing layers of the medical articles of the present invention be at least translucent and more preferably sufficiently transparent so that the wound site to which they are applied can be viewed through the medical article. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those describes in U.S. Pat. No. 4,499,896 (Heinecke); U.S. Pat. No. 4,598,004 (Heinecke); and U.S. Pat. No. 5,849,325 (Heinecke et al).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive that can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration -A-B-A- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and crosslinked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. No. 6,198,016 B1 (Lucast et al.), U.S. Pat. No. 6,518,343 (Lucast et al.) and U.S.

Pat. No. 6,441,092 (Gieselman); multilayered adhesives as disclosed in U.S. Pat. No. 6,461,467 (Blatchford et al.). A particularly preferred adhesive includes 15 wt-% acrylic acid, 15 wt-% methoxypolyethylene oxide 400 acrylate, 70 wt-% isooctyl acrylate, prepared according to Example 1 of U.S. Pat. No. 5,849,325 (Heinecke et al.).

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the gel layer, i.e. the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are POLYSLIK S-8004, 83 pound (135.4 g/m$^2$) bleached silicone release paper supplied by H.P. Smith Co., Chicago, Ill., and 80 pound (130.5 g/m$^2$) bleached two-sided silicone coated paper (2-80-BKG-157) supplied by Daubert Chemical Co., Dixon, Ill.

A wound dressing of the present invention may also include a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. No. 5,531,855 (Heinecke et al.) and U.S. Pat. No. 5,738,642 (Heinecke et al.).

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
|---|---|
| DMA | dimethyl acrylamide |
| MEAcAc | 2-(methacryloxyloxy)ethyl acetoacetate |
| MPEG(400)A | methoxy poly(ethyleneglycol) acrylate |
| PEGDA-1 | poly(ethyleneglycol) diacrylate ($M_n$ = 575 g/mol) |
| PEGDA-2 | poly(ethyleneglycol) diacrylate ($M_n$ = 258 g/mol) |
| DBU | 1,8 Diaza-bicyclo[5.4.0]undec-7-ene, used as a 1% by weight solution in THF |
| THF | Tetrahydrofuran |
| VAZO 52 | 2-(1-Cyano-1,3-dimethyl-butylazo)-2,4-dimethyl-pentanenitrile commercially available from DuPont Chemical Co.; Wilmington, DE |
| Liner | A 51 micrometer (2 mil) polyethylene terephthalate (PET) liner with silicone coating |

Test Methods

Percent Swell

Polymer films of approximately 25 mm$^2$ and 1 mm thick were weighed (dry weight) and then completely submerged into a 0.9% saline solution. The samples were removed after 24 hours, patted dry over the exterior surface, and reweighed (wet weight). The swell was calculated based of the formula:

(wet weight−dry weight)/dry weight×100%=% swell.

Preparative Example 1

Preparation of a linear co-polymer of poly(DMA)-co-(MEAcAc)

In a glass jar was placed DMA (37.5 grams), MEAcAc (37.5 grams), VAZO 52 (0.3 grams) and 75 grams of THF. The resulting solution was sparged with nitrogen for 20 minutes and then heated in a water shaker bath at 60° C. for approximately 16 hours to allow for polymerization.

Examples 1-3

Examples 1-3 were prepared with various amounts of the co-polymer poly(DMA)-co-(MEAcAc) prepared in Preparative Example 1, MPEG(400)A, PEGDA-1, and THF as shown in Table 1. The components were combined in a glass jar and allowed to form a uniform mixture in a shaker bath at 50° C. for approximately 18 hours. A 1% by weight stock solution of DBU (in THF) was added to the solution and the mixture was stirred with a wooden applicator stick. This mixture was poured onto a Liner and the solvent was allowed to evaporate at room temperature. The transparent films were cured at 70° C. for 7 hours and tested for percent swell using the test method described above. The films remained transparent after swelling.

TABLE 1

| Example | poly(DMA)-co-(MEAcAc) (grams) | MPEG (400)A (grams) | PEGDA-1 (grams) | THF (grams) | DBU stock soln. (grams) | % swell |
|---|---|---|---|---|---|---|
| 1 | 4.55 | 3.875 | 0.061 | 4.38 | 0.62 | 522 |
| 2 | 5.10 | 3.861 | 0.069 | 4.38 | 0.62 | 497 |
| 3 | 4.91 | 2.788 | 0.066 | 4.55 | 0.45 | 469 |

Examples 4-6

Examples 4-6 were prepared with various amounts of the co-polymer poly(DMA)-co-(MEAcAc) prepared in Preparative Example 1, MPEG(400)A, PEGDA-2, and THF as shown in Table 2. The components were combined in a glass jar and allowed to form a uniform mixture in a shaker bath at 50° C. for approximately 18 hours. A 1% by weight stock solution of DBU (in THF) was added to the solution and the mixture was stirred with a wooden applicator stick. This mixture was poured onto a Liner and the solvent was allowed to evaporate at room temperature. The transparent films were cured at 70° C. for 7 hours and tested for percent swell using the test method described above. The films remained transparent after swelling.

TABLE 2

| Example | poly(DMA)-co-(MEAcAc) (grams) | MPEG (400)A (grams) | PEGDA-2 (grams) | THF (grams) | DBU stock soln. (grams) | % Swell |
|---|---|---|---|---|---|---|
| 4 | 5.20 | 4.429 | 0.031 | 4.29 | 0.71 | 544 |
| 5 | 5.51 | 4.171 | 0.033 | 4.33 | 0.67 | 508 |
| 6 | 5.08 | 2.884 | 0.031 | 4.53 | 0.47 | 467 |

The invention claimed is:

1. An absorbent dressing comprising a hydrophilic gel absorbent layer comprising the reaction product of:
  a) a first component acrylate polymer comprising a plurality of polymerized monomer units having pendent hydrophilic poly(alkylene oxide) groups, and a plurality of polymerized monomer units having pendent Michael donor groups;
  b) a crosslinking agent comprising at least two Michael acceptor groups, and
  c) a monoacryl Michael acceptor component that is not a methacryl compound,
  wherein the ratio of Michael donor equivalents to total Michael acceptor group equivalents (of the crosslinking agent plus monoacryl compounds) is 1.2:1 to 1:1.2.

2. The absorbent dressing of claim 1 comprising:
  a permeable facing layer,
  a backing layer bonded to said facing layer at the periphery, and
  a hydrophilic gel absorbent layer disposed between the backing and facing layer.

3. The absorbent dressing of claim 2 having a layer of pressure sensitive adhesive on at least a portion of the front surface of the facing layer.

4. The absorbent dressing of claim 1 wherein the gel layer further comprises a pharmacologically active agent.

5. The absorbent dressing of claim 1 wherein the gel layer further comprises a hydrocolloid.

6. The absorbent dressing of claim 1 wherein the gel layer further comprises a patterned surface.

7. The absorbent dressing of claim 1, wherein said absorbent layer is transparent on swelling.

8. The absorbent dressing of claim 1 wherein said crosslinking agent comprises a polyacryl compound.

9. The absorbent dressing of claim 1 wherein said crosslinking agent comprises a hydrophilic poly(alkylene oxide) crosslinking agent having acryl terminal groups.

10. The absorbent dressing of claim 1 wherein said crosslinking agent is of the formula

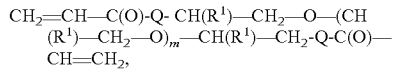

wherein $R^1$ is a H or a $C_1$ to $C_4$ alkyl group, and m is from 1 to 500, and Q is a divalent linking group selected from alkylene, —O—, —NR$^1$—, —S— and combinations thereof.

11. The absorbent dressing of claim 1, wherein said crosslinking agent is a poly(ethylene oxide) (co)polymer having terminal acryl groups.

12. The absorbent dressing of claim 1 wherein said first component polymer comprises:
  a) from 25 to 75 parts by weight of polymerized monomer units having pendent, hydrophilic groups,
  b) from 25 to 75 parts by weight of polymerized monomer units derived from of an ethylenically-unsaturated monomer having a pendent Michael donor groups;
  c) from 0 to 25 parts by weight of polymerized monomer units derived from acrylic acid esters of non-tertiary alkyl alcohols containing 1-14 carbon atoms.

13. The absorbent dressing of claim 1 which comprises:
  a) from 80 to 99.9 parts by weight of said first component polymer, and
  b) from 0.1 to 50 parts by weight of said crosslinking agent, wherein the composition, can absorb at least 50 wt. % water.

14. The composition of claim 1, wherein said monomer units having Michael donor groups are of the formula:

wherein
$R^4$ represents hydrogen, an alkyl group or an aryl group;
$W^1$ is selected from a cyano group, a nitro group, an alkyl carbonyl group, an alkoxy carbonyl group, an aryl carbonyl group, an aryloxy carbonyl group, an amido group, and a sulphonyl group,
Z is a polymerizable ethylenically unsaturated moiety, and
Q is a divalent linking group selected from alkylene, —O—, —NR$^1$—, —S—, and combinations thereof.

15. The absorbent dressing of claim 1 wherein said monomer units having pendent hydrophilic poly(alkylene oxide) groups are of the formula:

wherein Z is a polymerizable ethylenically unsaturated moiety, $R^1$ is a H or a $C_1$ to $C_4$ alkyl group, $R^2$ is a H, a $C_1$ to $C_4$ alkyl group, aryl group, or combinations thereof and n is from 2 to 100, and Q is a divalent linking group.

* * * * *

UNITED STATES PATENT AND TRADEMARK OFFICE
CERTIFICATE OF CORRECTION

PATENT NO. : 8,609,131 B2  
APPLICATION NO. : 11/042229  
DATED : December 17, 2013  
INVENTOR(S) : David Joshua Plaut Page 1 of 1

It is certified that error appears in the above-identified patent and that said Letters Patent is hereby corrected as shown below:

In the Specification:

Column 7,
Lines 46-47, delete "dimethylarcrylamide," and insert -- dimethylacrylamide, --.

Column 10,
Line 48, delete "isobomyl" and insert -- isobornyl --.

Column 12,
Line 52, delete "$R^5$independently" and insert -- $R^5$ independently --.

Column 13,
Line 55, delete "thicesters" and insert -- thioesters --.

Column 20,
Lines 15-16, delete "styrenetbutadiene" and insert -- styrene/butadiene --.

In the Claims:

Column 26,
Line 48, in claim 15, delete "$R^1$" and insert -- $R^1$ --.

Signed and Sealed this  
Twenty-fourth Day of June, 2014

Michelle K. Lee  
*Deputy Director of the United States Patent and Trademark Office*